United States Patent
Wostyn

(10) Patent No.: US 12,151,072 B2
(45) Date of Patent: Nov. 26, 2024

(54) CEREBROSPINAL FLUID DIVERSION FOR THE TREATMENT OF CHRONIC FATIGUE SYNDROME AND FIBROMYALGIA AND USE OF RNFL THINNING AS A BIOMARKER THEREFOR

(71) Applicants: Xavier Deklerck, Oostkamp (BE); Peter Wostyn, Oostduinkerke (BE)

(72) Inventor: Peter Wostyn, Oostduinkerke (BE)

(73) Assignees: Xavier Deklerck, Oostkamp (BE); Peter Wostyn, Oostduinkerke (BE)

( * ) Notice: Subject to any disclaimer, the term of this patent is extended or adjusted under 35 U.S.C. 154(b) by 1024 days.

(21) Appl. No.: 17/026,555

(22) Filed: Sep. 21, 2020

(65) Prior Publication Data

US 2021/0085936 A1    Mar. 25, 2021

Related U.S. Application Data

(60) Provisional application No. 62/904,060, filed on Sep. 23, 2019.

(51) Int. Cl.
   *A61M 27/00*    (2006.01)

(52) U.S. Cl.
   CPC ..... *A61M 27/006* (2013.01); *A61M 2027/004* (2013.01); *A61M 2202/0464* (2013.01); *A61M 2230/00* (2013.01)

(58) Field of Classification Search
   CPC .............. A61M 27/002; A61M 27/006; A61M 2027/004; A61M 2202/0464; A61M 2230/00
   See application file for complete search history.

(56) References Cited

U.S. PATENT DOCUMENTS

| | | | |
|---|---|---|---|
| 8,012,115 B2 * | 9/2011 | Karageozian | A61F 9/0017 604/8 |
| 2006/0020239 A1 | 1/2006 | Geiger et al. | |
| 2006/0111659 A1 | 5/2006 | Tyler | |
| 2010/0076336 A1 | 3/2010 | Stahmann et al. | |
| 2010/0076366 A1 * | 3/2010 | Henderson, Sr. | A61B 5/076 604/9 |
| 2013/0197422 A1 | 8/2013 | Browd et al. | |
| 2018/0125707 A1 * | 5/2018 | Khaderi | A61M 27/006 |
| 2018/0228970 A1 | 8/2018 | Wostyn | |
| 2019/0015001 A1 | 1/2019 | Wostyn | |
| 2019/0282792 A1 | 9/2019 | Wostyn et al. | |
| 2019/0290891 A1 | 9/2019 | Wostyn | |

OTHER PUBLICATIONS

Higgins et al., "Chronic Fatigue Syndrome and Idiopathic Intracranial Hypertension: Different Manifestations of the Same Disorder of Intracranial Pressure?," Medical Hypotheses, vol. 105, 2017, pp. 6-9.

(Continued)

*Primary Examiner* — Philip R Wiest
(74) *Attorney, Agent, or Firm* — Amster, Rothstein & Ebenstein LLP

(57) ABSTRACT

This application discloses methods and tools for the treatment of chronic fatigue syndrome (CFS) and fibromyalgia and the use of retinal nerve fiber layer thinning as a biomarker for the treatment.

16 Claims, 1 Drawing Sheet

(56) References Cited

OTHER PUBLICATIONS

Higgins et al., "Looking for Idiopathic Intracranial Hypertension in Patients With Chronic Fatigue Syndrome," Journal of Observational Pain Medicine, vol. 1, No. 2, 2013, pp. 28-35.

Higgins et al., "Lumbar Puncture, Chronic Fatigue Syndrome and Idiopathic Intracranial Hypertension: A Cross-Sectional Study," Journal of the Royal Society of Medicine—Short Reports, vol. 4, No. 12, 2013, pp. 1-7.

Wostyn et al., "Can Cerebrospinal Fluid Diversion Be Beneficial in the Treatment of Chronic Fatigue Syndrome?," Medical Hypotheses, vol. 118, Sep. 2018, e-published Apr. 24, 2018, p. 174.

Wostyn et al., "Fibromyalgia as a Glymphatic Overload Syndrome," Medical Hypotheses, vol. 115, Jun. 2018, pp. 17-18.

\* cited by examiner

A
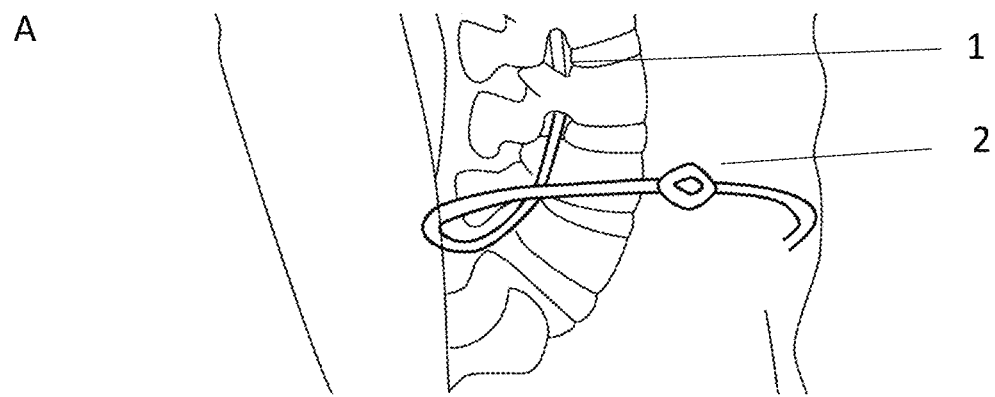
B
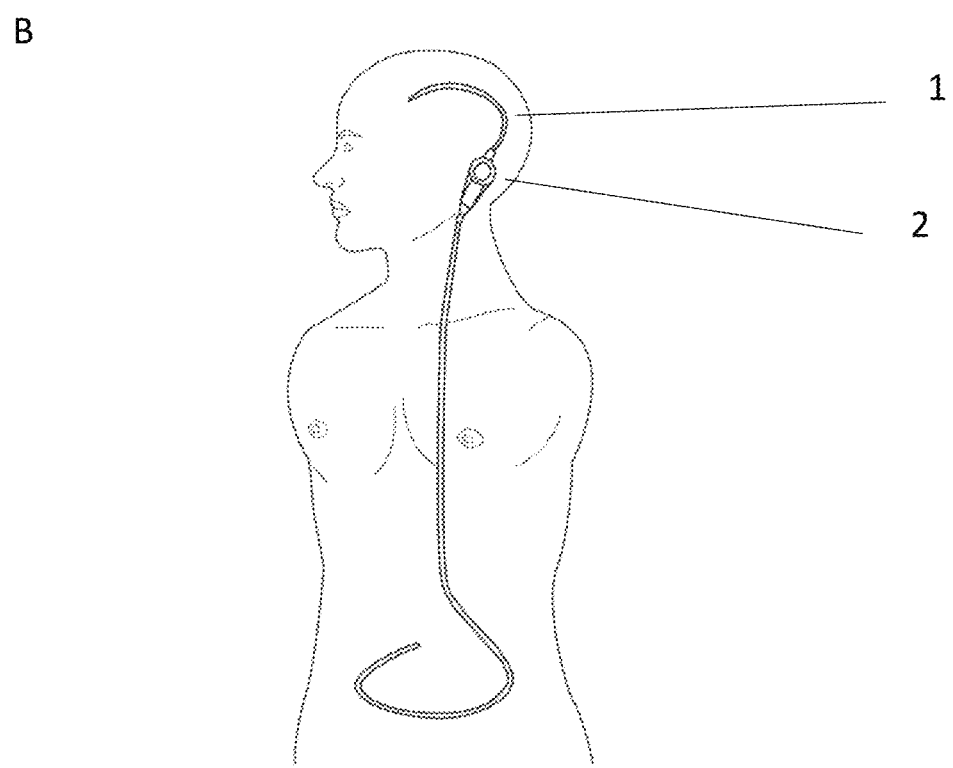

CEREBROSPINAL FLUID DIVERSION FOR THE TREATMENT OF CHRONIC FATIGUE SYNDROME AND FIBROMYALGIA AND USE OF RNFL THINNING AS A BIOMARKER THEREFOR

CROSS-REFERENCE TO RELATED APPLICATION

This application claims the benefit of U.S. Provisional Patent Application No. 62/904,060, filed on Sep. 23, 2019, the content of which is herein incorporated by reference in its entirety.

FIELD OF THE INVENTION

The invention relates to methods and tools for the treatment of chronic fatigue syndrome (CFS) and fibromyalgia and to the use of retinal nerve fiber layer thinning as a biomarker for the treatment.

BACKGROUND

Chronic fatigue syndrome (CFS) is a debilitating disorder characterized by extreme fatigue or tiredness which is not linked to an underlying medical condition. There are different theories about the causes of CSF, such as viral infection, psychological stress, weakened immune system, hormonal imbalance, and genetic predisposition, but no definite etiology.

There is also no specific cure for CFS. As the symptoms vary for different patients, treatment is developed based on the relieving symptoms of each individual patient. Similarly, fibromyalgia is a disease with an unknown etiology. The main characteristic is chronic widespread musculoskeletal pain and the treatment options are limited. There is a need for a treatment option for patients suffering from CFS and fibromyalgia that addresses a physiological cause of these diseases.

SUMMARY OF THE INVENTION

The present invention aims to address the need for a treatment which addresses a physiological cause of chronic fatigue syndrome (CFS) and fibromyalgia. The present invention is based on the observation that the accumulation of toxins in the brain will cause symptoms such as headaches, loss of memory and concentration, etc., which are typically experienced by patients diagnosed with CFS. Similarly, while not necessarily related in etiology, accumulation of toxins around the spinal system (in the dorsal root ganglia) will cause pains in different areas of the body, which are typically experienced by patients diagnosed with fibromyalgia.

While the focus of these diseases are quite different (i.e. pain in fibromyalgia vs. fatigue in CFS), the inventor proposes that accumulation of toxins in the brain and/or around the spine is the result of a dysfunction of the glymphatic system, which under normal conditions ensures clearance of interstitial waste. The paravascular glymphatic pathways support the clearance of solutes from the brain and spinal cord to the cerebrospinal fluid (CSF). It is therefore an object of the present invention to provide a treatment method which addresses the problem of toxic build up in the brain and spinal system. More particularly, the present invention provides in methods and tools which avoid toxic build up in the brain and/or spinal cord (spine) and/or dorsal root ganglia by diverting a fraction of the cerebrospinal fluid (CSF) from the cerebral ventricles and/or the spinal (e.g., lumbar) subarachnoid space. Such CSF diversion will unblock stagnation of glymphatic transport and promote waste clearance from the brain and/or spin and/or dorsal root ganglia to the CSF.

In addition, the inventor proposes that the diversion of CSF in these patients is particularly useful in patients that have retinal nerve fiber layer (also referred to herein as "RNFL") thinning. Indeed, studies have demonstrated that disrupting the function of aquaporin-4 which is involved in glymphatic clearance results in a loss of retinal ganglion cells (RGCs), a reduced RNFL, and accumulation of beta-amyloid in the retina (Song X Y, Wu W F, Gabbi C, et al. Proc Natl Acad Sci USA 2019; 116: 16507-12). While the authors do not make a functional connection, the inventor has identified that this is evidence of a direct link between reduced glymphatic clearance function and RNFL thinning. Thus, patients in which RNFL thinning is observed are patients which have a reduced glymphatic clearance function. As indicated above, the inventor proposes that dysfunction of the glymphatic system causes accumulation of toxins in the brain and/or around the spine, contributing to symptoms of both CFS and fibromyalgia. Thus, while RNFL thinning may occur in patients with glymphatic system dysfunction over time, it is clear that patients in which RNFL thinning is observed, are primary candidates to benefit from diversion of CSF as described herein. More particularly, the inventor has now found that RNFL can be used to identify patients suffering from CFS which would particularly benefit from CSF diversion. Accordingly, the invention provides methods of treating CFS in a patient, the method comprising diverting a fraction of CSF from the cerebral ventricles of said patient to a different location, thereby reducing the symptoms of CFS. Independently, the invention provides methods for treating fibromyalgia in a patient, the method comprising diverting a fraction of CSF from the spinal subarachnoid space of said patient to a different location, thereby reducing the symptoms of CFS or fibromyalgia.

Moreover, the invention provides methods which involve confirming glymphatic system dysfunction in a patient, more particularly in a patient suffering from symptoms of CFS, by determining whether said patient is suffering from RNFL thinning and optionally treating said patient suffering from RNFL thinning by CSF diversion using the method described above. Similarly, the invention provides methods which involve confirming glymphatic system dysfunction in a patient, more particularly in a patient suffering from symptoms of fibromyalgia, by determining whether said patient is suffering from RNFL thinning and optionally treating said patient suffering from RNFL thinning by CSF diversion using the method described above.

In particular embodiments of the methods of treatment provided herein, said fraction of CSF is diverted from the cerebral ventricles or the spinal subarachnoid space of said patient by a system which directs the flow of said fraction of CSF to a different location outside of the cerebrospinal cavity of said patient.

In particular embodiments of said method of treatment, the system is configured to direct the flow of said fraction of CSF from the cerebral ventricles of said patient to a different location in- or outside the body of said patient. In alternative embodiment, the system is configured to direct the flow of said fraction of CSF from the spinal subarachnoid space to another location in- or outside the body of said patient.

In further particular embodiments, of the methods of treatment provided herein said system is configured to ensure interstitial fluid drainage and/or avoid interstitial toxic build up.

In particular embodiments, the system is configured for the maintenance of a target volume of CSF in the ventricles of the brain or in the spinal subarachnoid space of said patient. In particular embodiments, the device comprises one or more valves which control the flow of CSF in the system. Additionally or alternatively, the system comprises a pump which controls the flow of CSF through said system.

In particular embodiments, the system comprises a sensing mechanism to determine the CSF volume, pressure and/or changes in the levels of toxins in CSF in said patient.

In particular embodiments, the pump and/or valve(s) are controlled by a microprocessor which is capable of converting a detector signal from the sensing mechanism into an effector signal which drives the pump and/or the valve(s).

In particular embodiments, the system comprises a shunt comprising a tube, a proximal catheter and a distal catheter.

In particular embodiments, the system is configured to transport CSF from the ventricles of the brain to a region outside the brain. In particular embodiments, the system is configured to transport CSF from the ventricles of the brain to the venous system of the brain. In particular embodiments, the system is configured to transport CSF from the spinal subarachnoid space to a region in-or outside the body. In particular embodiments, the system is configured to transport CSF to a region in the abdomen.

BRIEF DESCRIPTION OF THE DRAWINGS

FIG. 1A-1B depicts examples of devices for use in the present invention illustrating (A) a lumboperitoneal (LP) shunt suitable for diverting a fraction of CFS from the spinal subarachnoid space and (B) a ventriculoperitoneal (VP) shunt suitable for diverting a fraction of CFS from the cerebral ventricles to a different location, particularly the abdomen. (1) proximal catheter (2) proximal valve optionally comprising a pump, sensing mechanisms and/or a microprocessor.

DETAILED DESCRIPTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The present invention relates to methods and tools for treating chronic fatigue syndrome (CFS) or fibromyalgia by ensuring cerebrospinal fluid (CSF) drainage and avoiding interstitial toxic build up within the central nervous system. The present invention further provides devices suitable for carrying out these methods.

The inventor has found that the symptoms of CFS are at least in part caused by impaired glymphatic flow and toxic build up in the brain. In healthy patients, CSF that is produced from arterial blood by the choroid plexuses of the ventricles in the brain is absorbed into the venous or lymphatic system of the brain. CSF drains into the blood of venous sinuses through arachnoid villi and granulations. CSF also drains via nasal and dural lymphatics. In a number of diseased states however, there is a steady accumulation of interstitial waste products as a result of glymphatic dysfunction resulting from an overload in para-arterial CSF inflow and/or impaired paravenous outflow and/or fluid overload within the interstitial tissue. The latter may result from inflammation with resultant increased vascular permeability. Interstitial protein leakage, subsequently leading to accumulation of water driven by osmotic forces, could then contribute to glymphatic overload, ultimately creating stagnation of flow in the paravascular spaces and interstitium with subsequent accumulation of toxic substances. A dysfunctional glymphatic system in the brain can lead to a number of symptoms such as headaches, fatigue and loss of memory and concentration.

Similarly, a dysfunctional glymphatic system results in toxic build up in the spine and dorsal root ganglia. Accumulation of toxic substances close to the sensory neurons in the dorsal root ganglia can lead to pain in different areas of the body.

An important aspect of the invention thus relates to the treatment of impaired glymphatic flow and toxic build-up by improving CSF dynamics.

The term "toxic build-up" refers to the accumulation of toxins in a particular location. In the context of the present invention, the toxic accumulation occurs in the brain, and/or spinal cord and/or dorsal root ganglia. The term "toxin" as used herein refers to a compound which is detrimental to the health of its environment. More particularly in the context of the present invention, the toxins are "neurotoxins", i.e. compounds that are toxic for the functioning of the central nervous system. For instance, compounds such as B-amyloid (AB) have been associated with neurodegenerative disease and are considered as toxins. Typically the toxins present in the interstitial fluid represent toxic waste of the cells. In particular embodiments, the toxins are selected from B-amyloid (AB), tumor necrosis factor-alpha and nitric oxide.

In particular embodiments, the methods of the invention comprise diverting CSF from the cerebral ventricles. In more particular embodiments, the method comprises diverting a fraction of CSF from the cerebral ventricles of a patient by a system, which directs the flow of said fraction of CSF to a different location in- or outside the body of the patient. In further embodiments, the methods of the invention comprise diverting CSF from the spinal subarachnoid space. In more particular embodiments, the methods comprises diverting a fraction of CSF from the spinal subarachnoid space of a patient by a system, which directs the flow of said fraction of CSF to a different location in- or outside the body of the patient.

In particular embodiments, the methods of the present invention are of interest for the treatment of a patient suffering from chronic fatigue syndrome. The term "chronic fatigue syndrome", "CFS", "myalgic encephalomyelitis" or "ME" as used herein refers to a medical disorder characterized by long-term fatigue and other symptoms that limit a person's ability to carry out ordinary daily activities. Other symptoms may include, but are not limited to, sleep problems, joint pain or more generalized pains, headaches, sore throat, problems with thinking, remembering or concentrating, flu-like symptoms, dizziness and heart palpitations.

In particular embodiments, the methods of the present invention are of interest for the treatment of a patient suffering from fibromyalgia. "Fibromyalgia" as used herein refers to a medical condition characterized by chronic widespread musculoskeletal pain. Other symptoms include tiredness to a degree that normal activities are affected, memory loss, restless legs syndrome, bowel or bladder problems, and increased sensory sensitivity.

The term "treatment" refers to an alleviation of one or more symptoms of the disease. It will be understood by the skilled person, that given that the disease is characterized by symptoms, the present methods can also be considered to prevent CFS or fibromyalgia, as they aim to address the cause of the symptoms of these diseases, thereby reducing the likeliness of occurrence of these symptoms.

The present invention is particularly suited for the treatment of subjects or patients who are suffering from or are assumed to be suffering from CFS or fibromyalgia. In particular embodiments, the patients have been diagnosed as suffering from CFS or fibromyalgia. As the symptoms of CFS are common to other diseases, CFS is difficult to diagnose. Typically it involves identifying that the patient has at least four of the above-listed symptoms. The patient must typically suffer from severe fatigue that cannot be explained by other causes (e.g. antihistamines or alcohol) and cannot be cured by bed rest. The fatigue must last more than 6 months. In addition, the diagnosis may include ruling out that the patient is suffering from other diseases which have similar symptoms, such as a sleep disorder, mononucleosis, major depressive disorder, lyme disease, multiple sclerosis, lupus or hypothyroidism.

Similarly, the diagnosis of fibromyalgia involves verifying the characteristic symptoms, i.e. severe pain in three to six different areas of the body, or milder pain in seven or more different areas which has stayed at a similar level for at least three months, and ruling out other potential causes of these symptoms such as rheumatoid arthritis and multiple sclerosis. The present methods may also be of interest for patients suffering from symptoms common to both CFS and fibromyalgia, where neither of these diseases have been ruled out, or where the patient is potentially suffering from both diseases.

In some embodiments, the invention envisages determining whether or not the patient is suffering from thinning of the Retinal nerve fiber layer. The Retinal nerve fiber layer (RNFL) also referred to as nerve fiber layer or stratum opticum, is composed of axons originating from retinal ganglion cell neurons. These axons converge turning into the optic disc, cross the lamina cribrosa at the optic nerve head, and constitute the optic nerve. It is thickest near the optic disc, gradually diminishing toward the ora *serrata*. The thickness of different parts of the RNFL can thus be measured. For instance, the RNFL can be divided into different quadrants, the inferior quadrant, the superior quadrant, the nasal quadrant, and the temporal quadrant, each corresponding to 90° of the total circular surface. Alternatively, RNFL thickness can be measured in smaller sectors of the circle, such 12 equal sectors. Typically, absolute values of RNFL thickness are in micrometers. Preferably, the thickness is measured in more than one part of the Retinal nerve fiber layer. Alternatively or additionally, a single mean RNFL thickness for the full 360° scan can also be determined. The thickness of the RNFL can be quantified using noninvasive, rapid, objective, and reproducible ocular imaging technologies, such as optical coherence tomography (OCT), such as Cirrus OCT or Spectralis OCT. The thickness of the RNFL is considered reduced when a decrease is observed in at least one region of the RNFL compared to that of a control (healthy) patient. More particularly, the decrease compared to control is between 2-50 μm or at least 2 μm, preferably at least 5 μm, more particularly at least 10 μm, most particularly at least 15 μm or more. Alternatively, the thinning is expressed relative to the control as being at least 2%, preferably at least 3%, more preferably at least 5%, even more preferably at least a 10% decrease compared to control values. Absolute values for nerve fiber layer thicknesses for each sector of the eye may be influenced by one or more factors of the patient and the method of detection, such that preferably, the comparison is made between a patient and a comparable control using the same or a similar detection method. Retinal nerve fiber layer thickness varies significantly with age, ethnicity, axial length, and optic disc area. The mean RNFL thickness for the entire population has been reported to be 100.1 μm. Thinner RNFL measurements were associated with older age; being Caucasian, versus being either Hispanic or Asian; greater axial length; or smaller optic disc area. For every decade of increased age, mean RNFL thickness measured thinner by approximately 2.0 μm. Furthermore, glaucomatous optic neuropathy is characterized by thinning of the peripapillary RNFL as a result of axonal and secondary retinal ganglion cell loss. RNFL thinning is not specific to glaucomatous optic neuropathy and may also be seen in various non-glaucomatous optic neuropathies and neurodegenerative diseases, such as Alzheimer's disease, Parkinson's disease and multiple sclerosis.

The present invention envisages that draining a fraction of the CSF from the cerebral ventricles or the spinal subarachnoid space can unblock stagnation of glymphatic transport, improving interstitial fluid drainage and alleviating accumulation of toxins which cause chronic fatigue or pain. The phrase "a fraction of CSF" as used herein refers to an amount of CSF of which the drainage thereof is sufficient to partly or completely resolve impaired glymphatic flow, but does not induce intracranial hypotension.

In particular embodiments, the fraction of CSF is between 5-80%, such as between 10-75%, more particularly around 20-70% or 40-50% of the daily amount of CSF produced by a subject. In particular embodiments the fraction of CSF diverted is 0.1-20 ml/h, such as 3-15 ml/h, more particularly around 10 ml/h. Irrespective thereof, it is envisaged that the diversion of CSF can be ensured either constantly or only during discrete periods of the day such as for 1-18 h/day, or around 12 h/day. In particular embodiments the diversion is ensured only during the day. In particular embodiments, the fraction of CSF diverted is 10-400 ml/day, such as about 200 ml/day. The flow of CSF can be directed by one or more valves or pumps, as will be detailed herein.

In the methods of the present invention glymphatic dysfunction with toxic build-up within the interstitial fluid of the brain or within the spinal cord or dorsal root ganglia can be determined in a number of ways, more particularly based on a number of parameters. In a particular embodiment, the stagnated glymphatic flow with toxic build-up within the brain is determined indirectly by measuring the levels of one or more toxins in the CSF, such as can be determined by upon withdrawal of CSF. In particular embodiments, the level of toxins is compared to a standard. In further embodiments, the level of toxins is measured at different time points and is compared over time (e.g. at the start and after extended CSF withdrawal). In particular embodiments, the presence of toxins is determined by a lumbar puncture. Toxins must be cleared from the brain interstitium to the CSF compartment. Glymphatic dysfunction may impede this drainage of toxins from the interstitial fluid into CSF. This would result in higher concentrations of toxins lingering in the interstitial fluid rather than being transported into the CSF. Accordingly, according to the present invention, the presence of a reduced level of toxins in the CSF is indicative of impaired glymphatic clearance. As CSF withdrawal may unblock stagnation of glymphatic transport, the level of toxins in the CSF will increase due to the improvement of interstitial fluid flow. Therefore, a significant increase of toxins in the CSF in comparison with the CSF composition before/at the start of CSF withdrawal will confirm the occurrence of stagnated glymphatic flow in the patient.

In particular embodiments, the methods of the present invention comprise determining that the patient suffers from stagnated glymphatic flow prior to ensuring CSF diversion.

In particular embodiments, the step of determining that the patient suffers from stagnated glymphatic flow comprises measuring the levels of one or more toxins in the CSF of the patient. Typically, this measurement can be performed prior to or at the start of CSF withdrawal. Suitable methods for determining toxins in CSF include but are not limited to standard immunoassay, nephelometric assays, etc. For example, commercially available Enzyme Linked Immunosorbent Assay (ELISA) kits can be used to determine Aβ40 and Aβ42 levels in CSF. The level of the one or more toxins can be determined to be increased based on a threshold level (determined by measuring the level in the CSF of healthy patients) or based on previously measured levels in said patient.

In particular embodiments, the methods comprise determining the level of one or more toxins in the CSF at the start and at one or more intervals during CSF withdrawal. In particular embodiments, an increase in toxins during (at least the first phase of) CSF withdrawal is indicative of the fact that the CSF withdrawal unblocks stagnated glymphatic clearance. In particular embodiments, the level of toxins in the CSF will normalize after prolonged CSF diversion. However, in alternative embodiments, the level of toxins will remain at an increased level compared to the toxin level in the CSF prior to establishing the CSF diversion.

Additionally or alternatively, magnetic resonance imaging (MRI) brain scans, demonstrating dilated perivascular spaces can provide indirect evidence of stagnated glymphatic flow. The perivascular spaces have an important role in the homeostasis of cerebral fluids in the central nervous system. A correlation between perivascular space enlargement and a disturbance of CSF dynamics has been suggested. Indeed, if CSF outflow is reduced, local perivascular CSF recirculation may be impaired and, consequently, the perivascular spaces will dilate due to fluid retention. Indeed, small lesions indicative of perivascular space involvement have been observed on MRI scans of CFS patients (Hyde B. et al. Ontario: The Nightingale Research Foundation; 1992: Chapter 48, 425-31). Accordingly, in particular embodiments, the methods of the invention comprise determining the presence of dilated perivascular spaces in said patient. The presence of dilated perivascular spaces can be determined based on comparative measurements from healthy patients or based on previous measurements in said patient. In particular embodiments, the presence of dilated perivascular spaces is measured at regular intervals during treatment. In further particular embodiments, the diversion of CSF is continued if a reduction in dilated perivascular spaces is observed during treatment. Typically, the treatment is discontinued if no change in dilated perivascular spaces is observed. However, in particular embodiments, where the patient suffers from chronically dilated perivascular spaces, it may be that as a result of fibrosis, the dilation cannot recede, but that CSF diversion is still useful. Accordingly, where there is no change in dilated perivascular space, the presence of fibrosis should be checked.

Additionally or alternatively, it can be determined whether the patients suffer from RNFL thinning. The inventor suggests a correlation between RNFL thinning and a disturbance in glymphatic flow. As indicated above, RNFL thinning can be measured by optical coherence tomography (OCT). Accordingly, in particular embodiments, the methods of the invention comprise determining the presence of RNFL thinning in said patient. RNFL thinning can be determined based on comparative measurements from healthy patients or based on previous measurements in said patient.

Additionally or alternatively, glymphatic dysfunction associated with interstitial fluid accumulation can be detected indirectly by measuring intracranial pressure (ICP). An increase in ICP and volume are indicators for glymphatic fluid overload associated with increased toxic build-up. Accordingly, in particular embodiments, the sensing mechanism (additionally or alternatively) detects one or more parameters selected from CSF volume and CSF pressure in the brain, more particularly in the ventricles of the brain, or in the spinal subarachnoid space.

However, in particular embodiments, the methods of the present invention are of interest for the treatment of patients suffering from CFS or fibromyalgia who do not have an increase in intracranial pressure (ICP). Indeed the majority of patients suffering from CFS or fibromyalgia are believed not to suffer from a pathological increase in ICP.

As detailed herein, the present invention envisages the use of a system for diverting CSF in a patient. Suitable systems for use in the context of the present invention are known in the art. These are typically, shunt systems designed to drain cerebrospinal fluid from the brain ventricles or the spinal dorsal root ganglia to either the peritoneal cavity or the right atrium of the heart. In particular embodiments they are designed to function using the pressure differential between the brain and another part of the body and to regulate the drainage flow using a programmable valve and/or pump. Suitable systems may include but are not limited to the systems disclosed in WO2010112555, WO201800757, WO2017053451, US2016074638, CN201744055, which in some cases will need to be adjusted or set for the purposes as described herein. In particular embodiments, the system comprises a shunt. A shunt typically comprises a long tube with a proximal end (adapted for use in the target tissue) and a distal end (adapted for disposing the fluid).

In particular embodiments the system comprises one or more valves, which can be under control of a processor. Typically, the system comprises a proximal valve, to be placed in the target tissue such as the ventricle of the brain or the spinal subarachnoid space. Optionally, the system also comprises a distal valve, i.e. to be placed where the fluid is to be disposed. In particular embodiments, the valve is a one-way bypass valve. Further examples of suitable valves are known in the art and include, for instance US4551128, US20060089589. In further embodiments, the system does not comprise valves.

In particular embodiments, the system is configured to direct the flow of said fraction of CSF to a different location in-or outside the body of the patient, while not allowing flow-back of said fraction of CSF from the different location to the cerebral ventricles or the spinal subarachnoid space. The selected diversion site to which the CSF is diverted is not critical to the invention as long as it does not re-enter the cerebrospinal fluid system. In particular embodiments, the system allows the CSF to flow to the peritoneal space. The skilled person will understand that such a one-way flow can be achieved by introducing a one-way valve into the system.

In particular embodiments the system comprises a pump, which can ensure active pumping of CSF through the system, i.e. from the ventricles or the spinal subarachnoid space. In particular embodiments, the pump is preset to switch on/off at regular intervals.

In further particular embodiments the system comprises a microprocessor which controls the one or more valves and/or pump. In particular embodiments, the microprocessor is preset to switch on the pump based on one or more parameters or signals as detailed below.

In particular embodiments, the system further comprises a sensing mechanism which detects information on one or more parameters which information is processed by a processor to direct the action of the one or more valves and/or pump. In particular embodiments, the sensing mechanism can determine one or more parameters which can be used to direct the pump and/or valve. Additionally or alternatively, the sensing mechanism collects information as to the operability of the system (checking flow of CSF etc.). Suitable sensing mechanisms are known in the art and include but are not limited to the sensing mechanisms described in US20060020239.

In particular embodiments the sensing mechanism is an integral part of the system. In particular embodiments, the sensing mechanism is located at the proximal valve and is capable of sensing CSF pressure. Sensing mechanisms which are capable of detecting pressure are known in the art. For instance, the sensing mechanism can be based on inducing a pressure wave (such as generated by a pulsatile motion of the pump or valve). The pressure wave will travel into the ventricle and the rebounding pressure wave can be detected by an acoustic component (e.g. a piezoelectric membrane) in the wall of the valve. In particular embodiments, the detector signal of the sensing mechanism is directed to the (micro-)processor of the device where it can be interpreted. In particular embodiments, the detector signal is compared to a standard value. In further embodiments, the detector signal is monitored and subsequent signals are compared to determine significant deviations.

In further embodiments, at least part of the sensing mechanism is a sensor which is remote to the system, such as a sensor which is introduced into the brain independently from the system.

In particular embodiments, the microcontroller sends an effector signal to the pump and/or valve of the system to control the CSF flow. In particular embodiments, the microcontroller does not get input from a sensor system. In alternative embodiments, the microcontroller receives detector signals from the sensor system. In particular embodiments the detector signal received from the sensor of the system is compared by the microcontroller to pre-set value of the parameter, to determine whether or not an effector signal is to be sent to the pump and/or one or more valves. In these embodiments, the flow of CSF is initiated through the system when the sensor detects a value of one or more parameters which exceeds the threshold value for said parameters.

In particular embodiments, the system is configured to direct the flow of said fraction of CSF upon a predetermined level of one or more toxins in the CSF and/or a predetermined intracranial pressure.

In particular embodiments, the dependency on a predetermined intracranial pressure avoids intracranial pressure drops below a certain threshold or below the normal value for the patient concerned. Accordingly, In particular embodiments, the microprocessor determines that the CSF pressure is low if the intracranial pressure is below 5-15 mm Hg (7,5 en 20 cm $H_2O$), such as below 5 mm Hg. In further embodiments, the microprocessor determines that the ICP is low if it drops more than 10%, particularly more than 20% below the "normal" value for the patient. The "normal" value of ICP can be determined by performing a measurement before or at the start of CSF diversion. In particular embodiments, the "normal" ICP value is determined based on an average of several measurements. In particular embodiments, the "normal" ICP value is dependent on one or more factors such as time of day and body position.

In particular embodiments, the microprocessor determines that the CSF pressure or volume detected by the sensing mechanism is high it further directs the valve to open and/or the pump to pump CSF out of the ventricles or spinal cord. In particular embodiments, this can be for a predetermined amount of time. In further embodiments, the signal to the valve and/or pump can be maintained until a signal is obtained from the sensing mechanism that the parameter is normalized.

In particular embodiments, the system further comprises a reservoir for CSF sampling or injecting medications or dyes. The system may further comprise an on/off device, anti-siphon or other flow-compensating devices, or auxiliary catheters.

In particular embodiments, the system is designed to be able to administer artificial CSF to the target site. Indeed, where the diversion of CSF is expected to reduce intracranial pressure to levels which are at the lowest limit of acceptability, but amelioration of symptoms of CFS or fibromyalgia is, nevertheless, still absent or insignificant, it can be of interest to divert CSF while administering artificial CSF. In these embodiments, a pump is envisaged to control the inflow of artificial CSF to the target site.

The actual design of the system is not critical to the present invention. A generic design will typically comprise a tube (1) with a proximal catheter (3) comprising a proximal valve (5) and a distal catheter (4). The device will typically further comprise proximal anchoring means (5) with which the device can be anchored in the target area (e.g. in the brain close to the ventricles) and distal anchoring means (6) with which the device can be anchored at the diversion site. In particular embodiments, the system further comprises one or more valves (5) and/or a pump (6). The device further typically also comprises a sensor (7) and a microprocessor (8) which monitors the parameters detected by the sensor (7) and is coupled to the one or more valves (5) and/or pump (6) of the device. The device may also comprise a battery (8).

The device typically comprises a proximal catheter with a proximal valve, for insertion into the target site, which controls the inflow of CSF into the device. In particular embodiments, the valve is provided with holes for receiving the CSF fluid and is further adapted to resist the force required for the placement of the proximal end of the device into the target site and with structures which prevent clogging of the holes.

In particular embodiments, the system is configured to transport CSF from the ventricles of the brain to a region outside the brain. For instance, CSF can be diverted to the right atrium of the heart, to the pleural cavity or to the peritoneal cavity. In particular embodiments, the system is a ventriculoperitoneal shunt.

In particular embodiments, the system is configured to transport CSF from the ventricles of the brain to the venous system of the brain. In particular embodiments, the system is configured to transport the CSF from the ventricles to the venous system of the sagittal sinus of the brain or the venous system of the superior sagittal sinus of the brain (as described in US20060111659A1).

In particular embodiments, the system is configured to transport CSF from the spinal space, more particularly from the lumbar subarachnoid space, to the peritoneal cavity. In more particular embodiments, the system is a lumboperitoneal shunt.

In particular embodiments, the invention provides for a method for confirming glymphatic system dysfunction in a patient, more particularly in a patient suffering from symptoms of CFS or fibromyalgia. Indeed, these patients are particularly suitable for the treatment by CSF diversion as described herein. Thus these methods make it possible to determine or confirm the suitability of CSF diversion for said patients. In particular embodiments, the methods comprise determining that said patients suffer from RNFL thinning. In further particular embodiments these methods comprise determining said RNFL thinning by OCT, which has the advantage of being a non-invasive method. Thus, a non-invasive method can be used prior to confirm the envisaged advantage of the methods described herein.

In particular embodiments, the invention provides for methods of treatment of a patient suffering from symptoms of CFS or fibromyalgia, which methods involved determining whether said patient is suffering from RNFL thinning and, where the patient is determined to suffer from RNFL thinning, treating said patient by CSF diversion using the method described above. Indeed, the determination of RNFL thinning can be used as an additional criterium for determining the suitability of the treatment methods of the present invention.

In particular embodiments, the patients have been diagnosed as suffering from CFS or fibromyalgia.

In particular embodiments, the invention provides for selecting patients for treatment with CSF diversion as described herein, which methods comprise determining whether said patient is suffering from RNFL thinning, and where said determination confirms that said patient is suffering from RNFL thinning, selecting said patient for treatment with CSF diversion.

EXAMPLES

Example 1: Treatment of Patients Diagnosed with Chronic Fatigue Syndrome (CFS) to Ensure Reduced Toxic Build-Up in the Brain Five patients diagnosed with CFS are included in the study on the effect of CSF diversion on CFS-related symptoms. All patients provide written and oral informed consent before inclusion. The hospital's ethics committee approves the study protocol. The study is performed in accordance with the declaration of Helsinki.

Patients are included when they fulfill the Centers for Disease Control (CDC) diagnostic criteria for CFS. As recommended by the CDC criteria, patients can only be included when the body mass index is ≤40 kg/m². Main exclusion criteria are the presence of a somatic disease that could explain severe fatigue (eg., sleep apnea), psychiatric comorbidity (eg., depression) or the use of medication (with the exception of oral contraceptives and paracetamol).

After inclusion, patients receive external lumbar drainage (performed by a neurosurgeon) 10-15 ml/h over 72 h. After drainage, all patients are monitored for changes in the levels of toxins in CSF, intracranial pressure and symptoms of CFS. Fatigue is measured using the fatigue severity subscale of the checklist individual strength (CIS), which has been used frequently in CFS patients. Scores on the CIS-f can vary between 8 and 56, and a score ≥35 reflects severe fatigue. Psychological distress is measured with the total score on the Symptom Checklist-90 (SCL-90). CSF samples are collected from all patients prior to and immediately after the external lumbar drainage, and after 1 h, 6 h, 12 h, 24 h, 48 h, and 72 h of treatment. Commercially available Enzyme Linked Immunosorbent Assay (ELISA) kits can be used to determine Aβ40 and Aβ42 levels in CSF. Patients undergo intracranial pressure recordings via the lumbar drainage.

All patients show significant increases in CSF levels of Aβ40 and Aβ40 after lumbar drainage, suggesting improvement of drainage from the interstitial fluid space in the brain to the CSF. We find that the mean ICP in the group before lumbar drainage is towards the high end of normal, suggesting interstitial fluid accumulation associated with glymphatic dysfunction. All patients report an amelioration of CFS symptoms including fatigue, sometimes immediately after external lumbar drainage. Definitive CSF diversion, which consists of a lumbo-peritoneal shunt, is then performed in all patients. All patients report an amelioration of CFS symptoms including fatigue, sometimes immediately and at the latest one week after the placement of the shunt, which persists during the posttreatment follow-up period.

Example 2: Selection of Patients with Symptoms of CSF Suffering from RNFL Thinning for Treatment by CSF Diversion Patients characterized by symptoms of CFS are subjected to an analysis of the retinal nerve fiber thickness using OCT. Measurements are taken at the inner plexiform, nasal superior sector, nasal inferior sector, temporal inferior sector and temporal superior sector. The observations of RNFL thinning indicate the presence of glymphatic dysfunction. Those patients where in at least one sector RNFL thinning is observed of at least 2 μm compared to control, are selected for CSF diversion therapy. These patients are monitored for improvements in their symptoms.

The invention claimed is:

1. A method of treating a patient suffering from symptoms of chronic fatigue syndrome (CFS) or fibromyalgia, comprising the steps of (a) determining whether said patient is suffering from retinal nerve fiber layer (RNFL) thinning or receiving a determination that said patient is suffering from RNFL thinning, and (b) if said patient is suffering from RNFL thinning, diverting a fraction of CSF from the cerebral ventricles or the spinal subarachnoid space of said patient to a different location, thereby reducing or preventing the symptoms of CFS or fibromyalgia.

2. The method of claim 1, wherein said determination of RNFL thinning is performed by optical coherence tomography (OCT).

3. The method according to claim 1, which comprises providing said patient with a system which diverts said fraction of CSF to another location inside the body.

4. The method according to claim 3, wherein the system is configured to transport CSF to a region in the abdomen.

5. The method according to claim 1, which comprises providing said patient with a system which diverts said fraction of CSF to a location outside the body.

6. The method according to claim 1, which comprises providing said patient with a system which diverts said fraction of CSF to a location inside or outside the body, wherein the system comprises a proximal valve which controls the inflow of CSF into the system.

7. The method according to claim 1, which comprises providing said patient with a device which diverts said fraction of CSF to a location inside or outside the body wherein the system comprises a pump or valve which controls the flow of CSF through said system.

8. The method according to claim 7, wherein the system comprises a sensing mechanism to determine the CSF volume, pressure and/or changes in the levels of toxins in CSF of said patient.

9. The method according to claim 7, wherein, the pump and/or valve are controlled by a microprocessor which is capable of converting a detector signal from the sensing mechanism into an effector signal which drives the pump and/or the valve.

10. The method according to claim 9, wherein the sensing mechanism sends a detector signal to said microprocessor based on the detection of CSF pressure.

11. The method according to claim 9, wherein the sensing mechanism sends an effector signal to said microprocessor to ensure that the pump and/or valve ensure outflow of CSF from the target tissue.

12. The method according to claim 1, which comprises providing said patient with a system which diverts said fraction of CSF to a location inside or outside the body, wherein the system is configured to transport CSF from the ventricles of the brain to a region outside the brain.

13. The method according to claim 1, which comprises providing said patient with a system which diverts said fraction of CSF to a location inside or outside the body, wherein the system is configured to transport CSF from the spinal subarachnoid space.

14. The method according to claim 1, wherein the patient does not have an increased intracranial pressure (ICP) compared to a healthy patient.

15. A method of treating glymphatic system dysfunction in a patient comprising receiving a determination that said patient is suffering from glymphatic system dysfunction by determining whether said patient is suffering from retinal nerve fiber layer (RNFL) thinning, and diverting a fraction of CSF from the cerebral ventricles or the spinal subarachnoid space of said patient to a different location, thereby reducing symptoms of glymphatic system dysfunction in said patient.

16. The method of claim 15, wherein said determination of RNFL thinning is performed by optical coherence tomography (OCT).

* * * * *